United States Patent
Tombari et al.

(10) Patent No.: US 7,345,183 B2
(45) Date of Patent: Mar. 18, 2008

(54) PROCESS FOR OBTAINING NORELGESTROMIN IN DIFFERENT RELATIONS OF ISOMERS E AND Z

(75) Inventors: Dora Graciela Tombari, Buenos Aires (AR); Adriana Vecchioli, Ciudad Autónoma de Buenos Aires (AR)

(73) Assignee: Gador S.A. (AR)

( * ) Notice: Subject to any disclaimer, the term of this patent is extended or adjusted under 35 U.S.C. 154(b) by 249 days.

(21) Appl. No.: 10/877,858

(22) Filed: Jun. 25, 2004

(65) Prior Publication Data
US 2004/0266741 A1 Dec. 30, 2004

(30) Foreign Application Priority Data
Jun. 25, 2003 (AR) .............................. P030102267

(51) Int. Cl.
*C07J 41/00* (2006.01)
(52) U.S. Cl. .................................................. 552/520
(58) Field of Classification Search ................ 552/520
See application file for complete search history.

(56) References Cited

U.S. PATENT DOCUMENTS

| 3,532,689 A * | 10/1970 | Shroff .................... 540/106 |
| 4,027,019 A | 5/1977 | Shroff |
| 2005/0032763 A1 | 2/2005 | Tuba et al. |
| 2005/0032764 A1 | 2/2005 | Tuba et al. |

FOREIGN PATENT DOCUMENTS

CA 1122592 4/1982

OTHER PUBLICATIONS

NDA 21-180, 2001.*

* cited by examiner

*Primary Examiner*—Barbara P. Badio
(74) *Attorney, Agent, or Firm*—Defillo & Associates, Inc.; Evelyn A. Defillo

(57) ABSTRACT

The present invention is related to an oxime of the 13β-ethyl-17α-hydroxi-18,19-dinorpregn-4-en-20-in-3-o (norelgestromin) of Formula I with a relation of isomers E/Z between 1.3 and 1.6

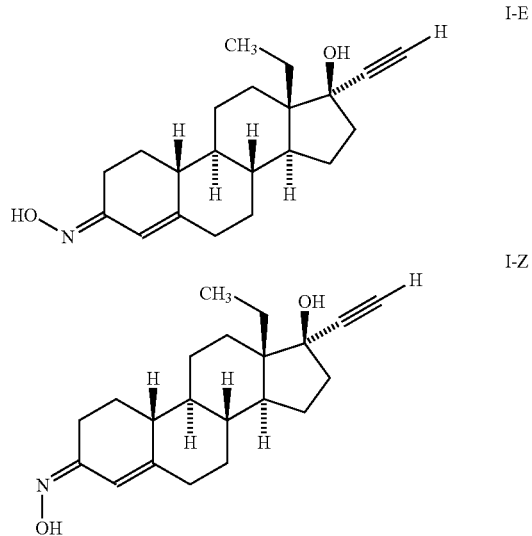

and the method of producing the oxime.

13 Claims, No Drawings

PROCESS FOR OBTAINING NORELGESTROMIN IN DIFFERENT RELATIONS OF ISOMERS E AND Z

FIELD OF THE INVENTION

The present invention refers to a method for obtaining, with good performance and quality, a product with distinct relations of the isomers E and Z of the oxime of 13β-ethyl-17α-hidroxy-18,19-dinorpregna-4-en-20-yn-3-one knows as norelgestromin of formulae I-E and I-Z respectively.

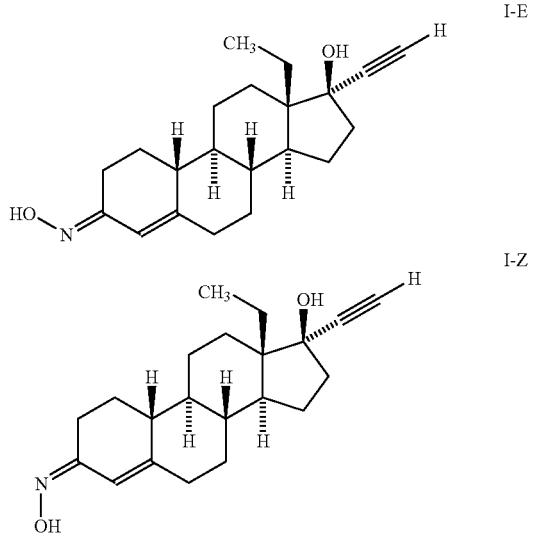

This substance, also known as 17-deacetyl norgestimate, has, as the same as norgestimate, utility in human medicine as progestogen and oral or transdermic anti-contraceptive.

BACKGROUND AND PRIOR ART

The existing bibliography shows that the norelgestromin is a product of the metabolism of the norgestimate, which results of the hydrolysis of the acetyl group in the 17th position. [S. Madden and D. J. Back -J. Steroid Biochem. Molec. Biol. 38 (4), 497 (1991); M. J. Wild et al. -ibid. 39 (4 A), 535 (1991); M. J. Wild et al. -ibid. 45 (5), 407 (1993)].

SUMMARY OF THE INVENTION

The prior art describes a method for obtaining norgestimate (Canadian Patent No. 1122592 issued Apr. 27, 1982 to Roussel Uclaf).

Even if this document teaches and claims a method for the preparation of norelgestromin, this document does not teach any structural form of the product neither the relation between the isomers E and Z.

Recently, the European Agency for the Evaluation of Medicinal Products (EMEA), published a document where was disclosed that Janssen/Cilag obtains the norelgestromin by hydrolysis of the norgestimate.

The Food and Drug Administration in its approval document No. NDA 21-180, belonging to ORTHO EVRA, accepts that there is documented evidence that proves that both isomers have the same therapeutic activity.

In the same document, said agency accepts, as an approval criteria of the substance, to have isomers relation anti/syn from 1.3 to 1.5. (FDA—Center for Drug Evaluation and Research—Application number 21-180—Chemistry Review), which is obtained by applying the procedure of EVRA.

The above mentioned procedure, uses norgestimate as raw material, substance that at the same time, is obtained from levonorgestrel by means of two additional synthetic steps, thus this method provides disadvantages for the direct synthesis of norelgestromin.

The most direct way for the preparation of norelgestromin, as it is the reaction of levonorgestrel with hydroxylamine, produces a product with a relation of isomers E/Z greater than 1.5 and, therefore, out of the rank accepted by the FDA.

Therefore, the object of the present invention is to provide a more simpler and direct way to produce norelgestromin which produces, in addition, a relation of isomers E/Z inside the range of 1.3-1.5.

The present process, is not only different from the process described in the document of EVRA and in the Canadian patent, but also presents advantages upon the same, and in addition, allows the regulation of the relation of isomers E and Z.

The differences and advantages of our process in view of the process described in the above prior art are:

Our process is a simpler procedure, since it employs as raw material levonorgestrel of the Formula II, which is a more economical and commercially accessible product than the 3,5-bis ethylendioxi-4,5-seco-13 β-ethy-17 β-hydroxi-17 α-ethynyl gonano of Formula III used by the Canadian patent and the

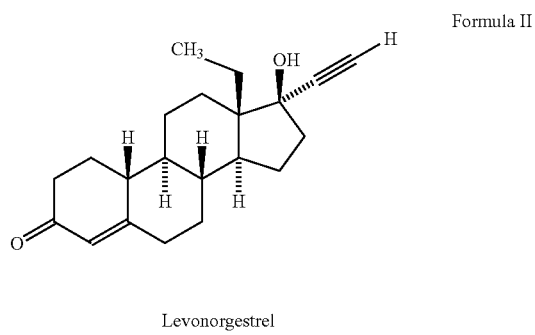

Levonorgestrel norgestimate of formula IV, as is described in the EMEA document.

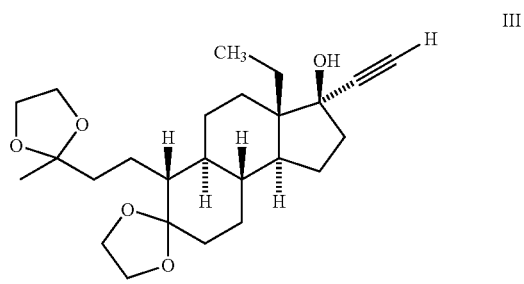

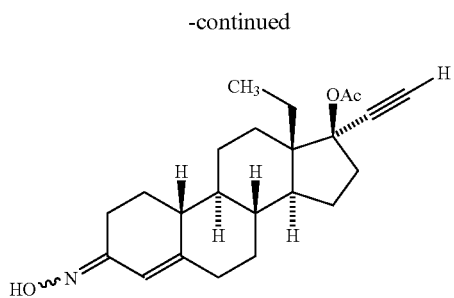

Norgestimate

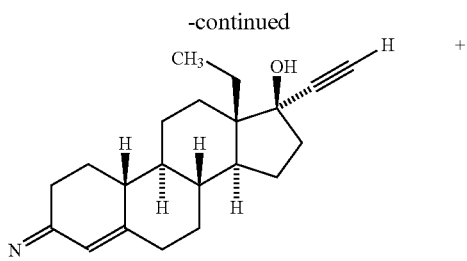

E

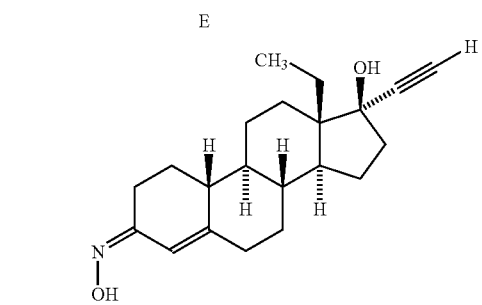

Z

Obtaining norelgestromin according to the process of the present invention includes a one step synthesis, instead of the three steps synthesis required by the process according to the cited Canadian patent.

Adding an acid, immediately after the formation of the oxime, allows obtaining different relations of isomers E/Z in a range from about 1.3 to 1.6, and therefore to fulfill the requirement of the American Agency.

In addition, the process according to the present invention allows obtaining an isomer E having a degree of purity greater than 99%.

The process described in the present invention allows obtaining a norelgestromin free of norgestimate, in which the main impurity is levonorgestrel that is the first metabolite of the norelgestromin.

DETAILED DESCRIPTION OF THE PRESENT INVENTION

The process for obtaining norelgestromin, including different relations of isomers E/Z, which is the object of the present invention, and which diagram is shown in the Figure I, comprises first generating hydroxylamine, by adding sodium acetate to a hydroxylamine salt in an alcohol medium having 1 to 4 atoms of carbon, preferably methanol.

FIG. I

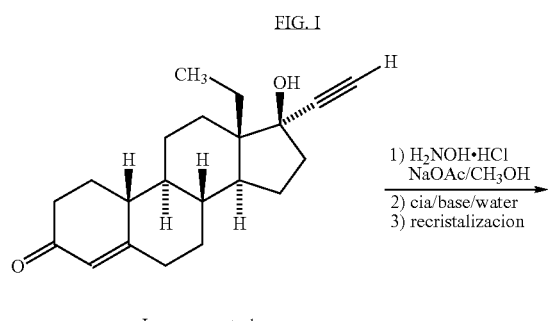

Levonorgestrel

1) H$_2$NOH·HCl NaOAc/CH$_3$OH
2) cia/base/water
3) recristalizacion

Levonorgestrel is added to the resultant suspension and the temperature maintained between 10° C. and the reflux temperature of the solvent during 10 to 40 minutes, preferably between 40° C. and the temperature of reflux of the solvent.

The reaction solvent is preferably methanol or isopropanol in a ratio from about 2 to 6 times the quantity of levonorgestrel. The molar ratio of hydroxylamine acetate to levonorgestrel is between 0.8 to 1.2, preferably 1.0 to 1.05.

Then an acid is added to the reaction medium to modify the acidity of the medium, the solution is left to rest from 20 to 120 minutes, preferably ½ to 1 hour at a temperature between 20 to 30° C.

The relation of isomers E/Z in the reaction medium can be modified by adding different amounts of acid, as well as exposition times as is shown in Tables I and II, so the relation E/Z, in the medium, can be between 1.3 to 1.6.

Due to the difference of solubility of the isomers in the hydro-alcoholic mediums employed for the precipitation, the isolated products have a proportion of E/Z greater than the one in the medium of reaction, which can reach values greater than the values show on Tables I and II.

It is therefore that, to maintain in the isolated product the relation E/Z in the range of 1.3-1.5, in reaction medium this relation should be, preferably, as lower as 1.5 as possible.

The acid is selected from proton inorganic acids such as hydrochloric acid, sulfuric acid, phosphoric acid, preferably hydrochloric acid, or organic acids such as toluenesulfonic acid, methanesulforic acid, monochloroacetic acid, preferably toluenesulfonic acid.

TABLE I

Variation of the relation E/Z in the reaction medium with the concentration of HCl

| Conc. HCl | $M_{HCL}/M_{Levonorg.}$ | E/Z | % Levonorgestrel |
|---|---|---|---|
| Control | — | 1.55 | — |
| 0.063 | 0.09 | 1.57 | 0.0186 |

TABLE I-continued

Variation of the relation E/Z in the reaction medium with the concentration of HCl

| Conc. HCl | $M_{HCL}/M_{Levonorg.}$ | E/Z | % Levonorgestrel |
|---|---|---|---|
| 0.125 | 0.17 | 1.54 | 0.0318 |
| 0.250 | 0.34 | 1.37 | 0.0668 |
| 0.500 | 0.69 | 1.28 | 0.1189 |

TABLE II

Variation of the relation E/Z in the reaction medium with the permanency time

| $M_{HCL}/M_{Levonorg.}$ | Time (min) | E/Z | % Levonorgestrel |
|---|---|---|---|
| 0.94 | Control | 1.50 | — |
| 0.94 | 30 | 1.4 | 0.1583 |
| 0.94 | 60 | 1.34 | 0.3171 |
| 0.62 | Control | 1.55 | 0.0511 |
| 0.62 | 30 | 1.38 | 0.1338 |
| 0.62 | 60 | 1.29 | 0.2471 |
| 0.31 | Control | 1.52 | — |
| 0.31 | 30 | 1.44 | 0.1150 |
| 0.31 | 60 | 1.40 | 0.1678 |

The molar ratio of acid regarding levonorgestrel is between 0.2 to 0.95, preferably between 0.4 to 0.8

Once the permanency time is completed in the presence of an acid, an organic base is added for the neutralization of the acid such as triethylamine, diethylamine, morpholine, preferably triethylamine, or an inorganic base such as hydroxides, carbonates, bicarbonates, alkaline metals phosphates or earth alkaline metal phosphates, preferably sodium bicarbonate or sodium hydroxide.

The solution is then filtered to a temperature greater than 25° C., to eliminate the salts.

This solution is then slowly overturned with agitation, over 2 to 5 volumes of water at a temperature between 0 to 30° C., preferably between 0 to 5° C.

The precipitate obtained from the raw norelgestromin is filtered and suspended in 3 to 6 times the mass of water regarding the weight of the wet product.

Then it is filtered, the previous step is repeated, and the product dried at 30-90° C.

The raw product is recrystallized in a polar aprotic solvent, chosen from the group of acetonitrile, dimethylformamide, acetone, ethyl acetate, preferably acetonitrile.

In addition, the product can be recrystallized in mixtures of the solvents, as well as mixtures of these aprotic polar solvents, with alcohols having 1 to 4 atoms of carbon or with water, preferably a mixture of acetonitrile with methanol.

In this way, a norelgestromin is obtained that does not contain norgestimate as impurity, with a suitable degree of purity that allows its use in human medicine.

If it is required to obtain a pure isomer E, then during the reaction solution, once the salts are filtered, the solvent is changed for a non-polar solvent, the solution is then distilled under reduced pressure, and the precipitate is filtered and dried.

As follows, like illustrative examples, not limiting the scope of the present invention, the following examples are included.

EXAMPLES

Example 1

Norelgetromin E/Z=1.6

In a 3 liter flask, equipped with agitation, heating and refrigerant for reflux, 900 ml of methanol were placed.

Then was added, with agitation, hydroxylamine hydrochloride (70 g) and sodium acetate anhydrous (83 g).

Next, levonorgestrel (300 g) was added and keeping the agitation, was heated to reflux during 30-40 minutes.

To the hot solution, triethylamine (92 ml) was added very slowly and with agitation.

The resultant suspension was filtered, and the precipitate washed with hot methanol (90 ml).

This solution was poured, slowly and with agitation, over cold water (3.3. l), chilled to 0-5° C. maintaining during the operation a temperature lower than 15° C.

Then after the aggregate is finished, it was chilled to 0-5° C. for one hour.

The suspension was then filtered, the precipitate was washed with cold water, and the solid was suspended in water (1.2 l) with agitation.

This last step was repeated.

The raw norelgestromin obtained was dried at 60-70° C., and the acetonitrile was re-crystallized concentrating the resultant solution by distillation under reduced pressure until half of its initial volume.

The pure norelgestromin was dried at 60-70° C. until constant weight.

263.8 g of the product were obtained (84%) with a title of 99.8% which was suitable for its use in human medicine.

The relation of isomers E/Z, determined by $^1$H-RMN, was of 1.6 and the rotating power $[\alpha]^{25}_D$=+45°. (Sol. 1% in CHCl$_3$).

The spectrum of $^1$H-RMN (CDCl$_3$) presented the following characteristic: 0.99 (t, 3 H, CH$_3$); 1.50 (m, 2 H, —CH$_2$— of the ethyl); 2.59 (s, 1 H, —C≡CH); 5.87 (s, 1 H, C$^4$—H isomer E) 6.55 (s, 1 H, C$^4$—H isomer Z).

Example 2

Norelgestromin E/Z=1.4

In a three neck flask with a 500 ml capacity, equipped with heating, agitation, and refrigerant for reflux, hydroxylamine hydrochloride (11.7 g), sodium acetate anhydrous (13.8 g) and methanol (100 ml) were added.

After 10 minutes of agitation, levonorgestrel (50 g), methanol (100 ml) were added, and heated with reflux during 30 minutes.

The solution was cooled down to room temperature, and concentrated HCl (8.3 ml) was added with agitation for 1 hour.

Then solid sodium hydroxide was added (8 g), and the mixture was agitated for 5 minutes; the pH of the suspension was 6.

The suspension was filtered to retain the salts, the precipitate was washed with methanol, and the resultant solution was poured, slowly and with agitation, over water (630 ml) at a temperature between 0-5° C.

The solution was filtered, and the wet solid was suspended in water (525 ml). The product was again filtered, and the previous step was repeated.

The precipitate was dried in an oven with an air current between 60-90° C. until the humidity value, determined by Karl Fischer, was ≦20%.

62.1 g of the raw product were obtained with 19.9% of humidity and a relation of isomers E/Z=1.31, which was re-crystallized with acetonitrile at reduced pressure until incipient crystallization.

45.5 g of a product were obtained (86.8%) with a title of 99.2%.

The relation of isomers E/Z, determined by $^1$H-RMN, was of 1.46 and the power rotator $[\alpha]^{25}_D=+40°$. (Sol. 1% in CHCl$_3$).

Example 3

Norelgestromin—Isomer E

In a 250 ml flask, equipped with agitation, heating and refrigerant for reflux, 80 ml of methanol were placed.

Then was added, with agitation, hydroxylamine hydrochloride of (4.67 g) and sodium acetate anhydrous (5.5 g).

Next, levonorgestrel (20 g) was added and keeping the agitation was heated to reflux during 30-40 minutes.

The resultant suspension was filtered; the precipitate was then washed with hot methanol (5 ml).

This solution was distilled at a reduced pressure of 45-55° C., toluene was added during this step, thus all the methanol was replaced by toluene.

The solution was then cooled down at room temperature and maintained to 0-5° C. during about 15 hours.

The suspension was filtered, and the precipitate washed with cold toluene.

Then the precipitate was dried in a vacuum oven at 50° C. until constant weight.

10.98 g of a product were obtained (52.4%) which showed to be the isomer E with 96% of isomeric purity (HPLC), the value of related substances, by this method, was 0.11%.

The spectrum of $^1$H-RMN (CDCl$_3$) presented the following characteristic: 0.99 (t, 3 H, CH$_3$); 1.50 (m, 2 H, —CH$_2$— of the ethyl); 2.59 (s, 1 H, —C≡CH); 5.87 (s, 1 H, C$^4$—H isomer E).

What is claimed is:

1. The process for producing an oxime of the 13 β-ethyl-17 α-hydroxy-18,19-dinorpregna-4-en-20-yn-3-one (norelgestromin) of Formula I with a relation of isomers E/Z between 1.3 and 1.6 comprising:

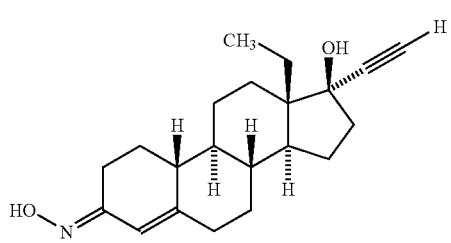

I-E

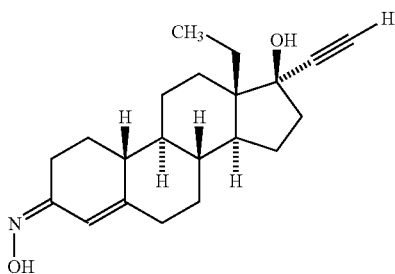

I-Z a) producing hydroxylamine by adding an acetate salt to a hydroxylamine salt in a solvent medium;
b) adding levonorgestrel to the solution of step a to produce an oxime;
c) adding an acid to modify the acidity of the solution of step b; and
d) adding a base to neutralize the solution.

2. A process according to claim 1, further comprising filtering the formed salt on step d and diluting the solution with water.

3. A process according to claim 2, further comprising precipitating the product in a polar solvent, alcohol, water, or mixture thereof.

4. A process according to claim 3, further comprising drying the product until constant weight.

5. A process according to claim 1, wherein the solvent is an alcohol in a molar ratio of solvent to levonorgestrel of 2 to 6.

6. A process according to claim 1, wherein a molar ratio of the hydroxylamine to levonorgestrel is between 0.8 and 1.2.

7. A process according to claim 1, wherein a molar ratio of the hydroxylamine to levonorgestrel is 1.0 to 1.05.

8. A process according to claim 5, wherein the alcohol is selected from methanol or isopropanol.

9. A process according to claim 1, wherein the acid is chosen from the group of hydrochloride acid, sulfuric acid, phosphoric acid, toluenesulfonic acid, methanesulfonic acid, or monochloroacetic acid.

10. A process according to claim 1, wherein the base is chosen from triethylamine, diethylamine, morpholine, hydroxides, carbonates, bicarbonates, alkaline metals phosphates or earth alkaline metal phosphates.

11. A process according to claim 1, wherein the product obtained does not contain norgestimate.

12. A process according to claim 1, wherein the molar ratio of acid to levonorgestrel is between 0.2 and 0.95.

13. A process according to claim 3, wherein the re-crystallization solvent is selected from the group of acetonitrile, dimethylformamide, acetone, ethyl acetate, isopropanol, methanol, water, or mixtures thereof.

* * * * *